(12) United States Patent
Kitamura et al.

(10) Patent No.: US 6,441,160 B2
(45) Date of Patent: *Aug. 27, 2002

(54) SEPARATING PLASMIDS FROM CONTAMINANTS USING HYDROPHOBIC OR HYDROPHOBIC AND ION EXCHANGE CHROMATOGRAPHY

(75) Inventors: Takashi Kitamura, Kumage-machi; Shigeru Nakatani, Shinnanyo, both of (JP)

(73) Assignee: Tosoh Corporation, Shinnanyo-shi (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/309,599

(22) Filed: May 11, 1999

(30) Foreign Application Priority Data

May 11, 1998 (JP) .......................... 10-127665

(51) Int. Cl.⁷ .......................... C07H 21/00; C12P 19/30; C12P 19/34

(52) U.S. Cl. .......................... 536/25.4; 435/89; 435/91.1; 536/25.41

(58) Field of Search .................. 435/89, 91.1; 536/25.4, 536/25.41

(56) References Cited

U.S. PATENT DOCUMENTS

| | | | | |
|---|---|---|---|---|
| 3,983,299 A | * | 9/1976 | Regnier | 428/405 |
| 4,935,342 A | | 6/1990 | Seligson et al. | 435/6 |
| 5,019,270 A | * | 5/1991 | Afeyan et al. | 210/656 |
| 5,057,426 A | | 10/1991 | Henco et al. | 435/270 |
| 5,561,064 A | | 10/1996 | Marquet et al. | 435/320.1 |
| 5,591,841 A | | 1/1997 | Ji et al. | 536/25.4 |
| 5,707,812 A | | 1/1998 | Horn et al. | 435/172.1 |
| 6,087,491 A | * | 7/2000 | Tang et al. | 536/25.4 |

FOREIGN PATENT DOCUMENTS

| | | | |
|---|---|---|---|
| WO | 9601268 | * | 1/1996 |
| WO | WO 96/02658 | | 2/1996 |

OTHER PUBLICATIONS

Dornburg et al., "Purification of high molecular weight RNAs and DNAs by HPLC", *Liquid Chromatogr.* 4(1):22–29 (1986).

Thompson, "A Review of High–Performance Liquid Chromatography in Nucleic Acids Research, III. Isolation, Purification, and Analysis of Supercoiled Plasmid DNA", *Bio Chromatography* 1(2):68–80 (1986).

Horn et al., "Cancer Gene Therapy Using Plasmid DNA: Purification of DNA for Human Clinical Trials", *Human Gene Therapy*, 6:565–573 (1995).

Caplen et al., "Gene therapy for cystic fibrosis in humans by liposome–mediated DNA transfer: the production of resources and the regulatory process", *Gene Therapy*, 1:139–147 (1994).

Lev, "A Procedure for Large–Scale Isolation of RNA–free Plasmid and Phage DNA without the Use of RNase", *Anal. Biochem.*, 160:332–336 (1987).

* cited by examiner

Primary Examiner—David M. Naff
(74) Attorney, Agent, or Firm—Jacobson Holman, PLLC

(57) ABSTRACT

Long chain nucleic acids such as plasmids are separated from contaminants including protein, RNA, DNA and mixtures thereof by using hydrophobic interaction chromatography or hydrophobic interaction chromatography and ion exchange chromatography. To carry out hydrophobic interaction chromatography, first and second columns containing first and second column materials are used. The first column material adsorbs protein and RNA at a salt concentration at which plasmid is not adsorbed to produce an eluate containing plasmid and DNA. The second column material adsorbs plasmid and DNA from the eluate at a salt concentration which the first column material adsorbs protein and RNA but not the plasmid. The plasmid is eluted from the second column material at a salt concentration at which plasmid is eluted. A tandem column may be formed by connecting in series the first and second columns. The connection between the columns is broken before eluting plasmid from the second column material. Ion exchange chromatography is carried out in addition to the hydrophobic interaction chromatography by adsorbing plasmid from an eluate from the second column material onto an ion exchange chromatography material, and eluting the adsorbed plasmid.

16 Claims, 4 Drawing Sheets

SEPARATING PLASMIDS FROM CONTAMINANTS USING HYDROPHOBIC OR HYDROPHOBIC AND ION EXCHANGE CHROMATOGRAPHY

BACKGROUND OF THE INVENTION

The present invention relates to a method for separating and purifying nucleic acids to be used for the genome analysis or the gene manipulation. In more detail, it relates to a method for separating long chain nucleic acids represented by particular DNA contained in the cells of animals, human, etc. that are effective for the gene therapy to be utilized for the therapy of genetic disease etc. due to DNA abnormality, by utilizing liquid chromatography, for example, plasmids, in the bacteria, organelle DNA, phage DNA, etc.

In recent years, the gene therapy is attracting an attention, and a method for separating and purifying a large quantity of long chain nucleic acids such as plasmids and DNA fragments to be used for gena therapy in simpler way and in shorter time is desired eagerly.

Here, for using nucleic acids for the therapy of human, it is desirable that the nucleic acids can be separated and purified keeping the same structure (higher-order structure) as that when they exist in organisms. Here, since the enzyme reaction is utilized for the recombination of nucleic acids, the nucleic acids are required to have been separated and purified to the extent that they can become the substrate for reaction. Also, in order to avoid the adverse effect of impurities on human body, the nucleic acids are required to have been separated and purified up to high purity.

For separating and purifying long chain nucleic acids such as DNAs and plasmids contained in the cells and bacteria, chemical treatment methods have been used most frequently, so far.

Among various long chain nucleic acids used for the gene therapy, in particular, plasmid is currently utilized in many cases, because of limited cleavage sites by particular restriction enzyme and relatively easy recombination manipulation. In the following, a general example of purifying a plasmid from *Escherichia coli* will be shown.

First, the cell wall is digested by treating with lysozyme for a short time, and RNase to degrade RNAs of *Escherichia coli* is added. Next, a mixed solution of NaOH and sodium dodecylsulfate (SDS) is added for the purpose of dissolving the cytoplasmic membrane. NaOH partially denatures DNAs and partially degrades RNAs and SDS acts to dissolve the membrane and denature proteins. Successively, SDS-protein complex and cell debris are precipitated by adding 5N potassium acetate (pH 4.8). At this time, pH is important for both to neutralize NaOH used in said manipulation and to renature plasmid. Thereafter, centrifugation is applied to remove the precipitates, thus obtaining aiming plasmids in supernatant.

In a series of these manipulations (hereinafter referred to as pretreatment process), it is important to mix slowly and firmly. If adding violent vibration during this manipulation, then the bacterial chromosomal DNA is cut off to small fragments so that they cannot aggregate, causing them to contaminate the plasmid.

Successively, isopropanol is added to the supernatant, and the mixture is centrifuged to precipitate and concentrate plasmids. Finally, protein is removed from plasmid fraction by precipitating with phenol and chloroform, and plasmid is precipitated with alcohol.

Through a series of manipulations as described above, it is possible to obtain plasmid with relatively high purity (hereinafter, said method of separating and purifying nucleic acid is referred to as chemical separating method). However, with the chemical separating method, separating and purifying process is complicated and a large quantity of organic solvent must be used, hence it poses many problems of treatment of waste solvents and others.

Besides the chemical separating and purifying method, there is a method of separating plasmids by electrophoresis. This method is a technique having the highest resolution at the moment. The electrophoretic method includes paper electrophoresis and gel electrophoresis, and gel electrophoresis is common currently. The electrophoretic method has an advantage of obtaining plasmid with very high purity, while it has many problems of long separation time, difficult collection, low sample loading, etc. Consequently, it is a present situation that the electrophoretic separation is used only when the purity of plasmid fraction purified by said chemical separating and purifying method is desired to improve further.

For solving the problems in chemical separating and purifying method and electrophoretic separation as explained above, a method of separating and purifying nucleic acids that utilizes liquid chromatography has been used recently. So far, there are examples, wherein long chain nucleic acids such as plasmids were separated and purified by using ion exchange chromatography and reversed phase chromatography.

With the method of separating and purifying nucleic acids utilizing liquid chromatography, there are good points of simple manipulation compared with chemical separating method, easy collection of nucleic acids and no necessity of using organic solvent etc. With said conventional method using ion exchange chromatographic method or reversed phase chromatographic method alone, however, there is a problem that the nucleic acids with sufficiently high purity, in particular, long chain nucleic acids such as plasmids cannot be obtained in large quantity.

Therefore, the invention aims at providing a separating method that utilizes liquid chromatography, which enables to separate a large quantity of long chain nucleic acids such as plasmids and DNAs in a shorter time.

SUMMARY OF THE INVENTION

The invention of claim 1 of the present application having been made in view of the purpose aforementioned provides a method of separating nucleic acids characterized by using hydrophobic interaction chromatography. And, the invention of claim 7 of the present application provides a method for separating and purifying nucleic acids characterized by using hydrophobic interaction chromatography and ion exchange chromatography in combination.

EXAMPLE 2

Figure 1:
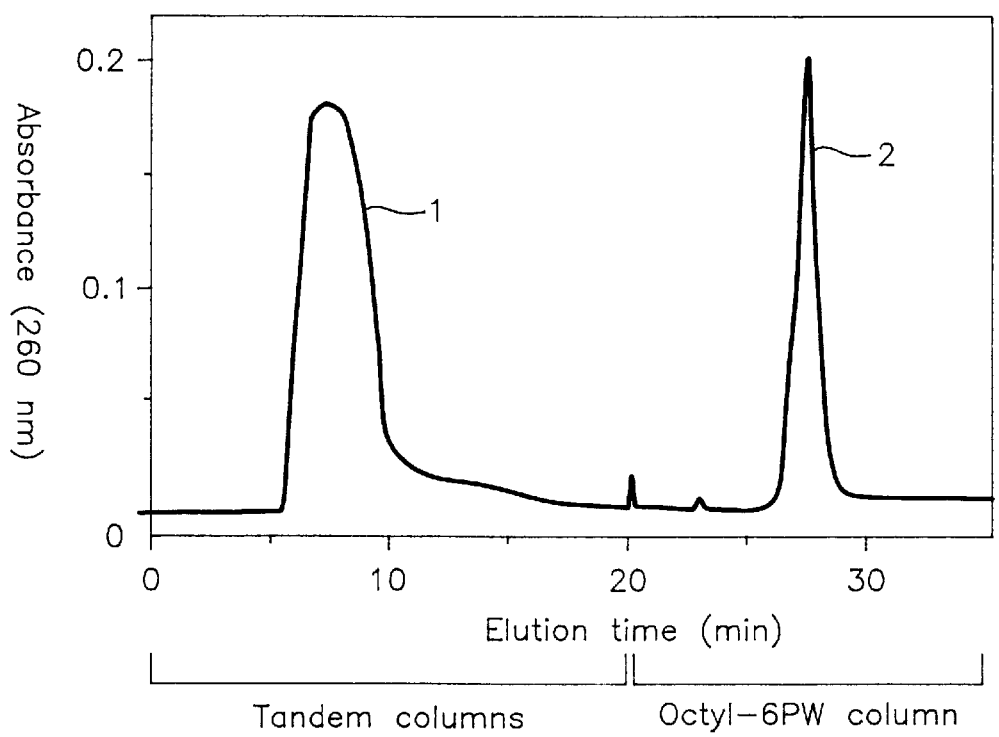
FIG. 1 is a chromatogram showing the result of separating a cleared lysate of *Escherichia coli* by means of hydrophobic interaction chromatography in Example 1.

In Figures,

| numeral 1 | peak of impurities |
| numeral 2 | peak of plasmid-fraction |
| numeral 3 | DNA size marker |
| numeral 4 | plasmid-fraction obtained by comparative Example 1 |
| numeral 5 | plasmid-fraction obtained by Example 1 |
| numeral 6 | commercial purified plasmid |

DETAILED DESCRIPTION OF THE INVENTION

In following, the invention will be illustrated in detail on the case of separating and purifying a plasmid being a long chain nucleic acid from *Escherichia coli* cultured in large quantity as an example. In such case, the inventive methods are useful for separating and purifying nucleic acids such as plasmids and DNAs being aiming products.

Compound to be used for the synthesis of base materials that are used for the packing material for hydrophobic interaction chromatography and ion exchange chromatography to be used in the invention may be any compounds, if various functional groups that exhibit hydrophobicity or various ion exchange groups can be introduced by a post-reaction after the base materials were synthesized in both cases. For example, as monofunctional monomers, styrene, o-halomethylstyrene, m-halomethylstyrene, p-halomethylstyrene, o-haloalkylstyrene, m-haloalkylstyrene, p-haloalkylstyrene, α-methylstyrene, α-methyl-o-halomethylstyrene, α-methyl-m-halomethylstyrene, α-methyl-p-halomethylstyrene, α-methyl-o-haloalkylstyrene, α-methyl-m-haloalkylstyrene, α-methyl-p-haloalkylstyrene, o-hydroxymethylstyrene, m-hydroxymethylstyrene, p-hydroxymethylstyrene, o-hydroxyalkylstyrene, m-hydroxyalkylstyrene, p-hydroxylalkylstyrene, α-methyl-o-hydroxymethylstyrene, α-methyl-m-hydroxymethylstyrene, α-methyl-p-hydroxymethylstyrene, α-methyl-o-hydroxyalkylstyrene, α-methyl-m-hydroxyalkylstyrene, α-methyl-p-hydroxyalkylstyrene, glycidyl methacrylate, glycidyl acrylate, hydroxyethyl acrylate, hydroxymethacrylate, vinyl acetate, etc. can be exemplified.

Here, as examples of haloalkyl groups substituted on aromatic ring, halogens such as Cl, Br, I and F and straight chain and/or branched saturated hydrocarbons with carbon atoms of 2 to 15 are mentioned.

As polyfunctional monomers, divinylbenzene, trivinylbenzene, divinyltoluene, trivinyltoluene, divinylnaphthalene, trivinylnaphthalene, ethylene glycol dimethacrylate, ethylene glycol diacrylate, diethylene glycol dimethacrylate, diethylene glycol diacrylate, methylenebismethacrylamide, methylenebisacrylamide, etc. can be exemplified.

As described above, for the compounds to be used in the invention, there is no special restriction, provided it is possible to introduce various functional groups that exhibit hydrophobicity or various ion exchange groups by the post-reaction, but, in order to minimize the influence on aiming products desired to separate due to the hydrophobicity exhibited by the base material itself, or the swelling or shirinking of the base material itself due to the change in salt concentration and the change in pH value, it is particularly preferable to prepare the base material using relatively hydrophilic monomers, for example, glycidyl methacrylate, glycidyl acrylate, hydroxyethyl acrylate, hydroxymethacrylate, vinyl acetate, etc.

How to commonly make the base material using said monomers is as follows (how to make the base material is not confined to a method shown here):

First, monofunctional monomer and polyfunctional monomer are weighed out at an appropriate ratio and precisely weighed-out diluent (solvent used for the purpose of adjusting the pores in particles formed) and similarly precisely weighed-out polymerization initiator are added, followed by well stirring. And, the mixture is submitted to so-called oil-in-water type suspension polymerization wherein the mixture is added into an aqueous solution dissolved suspension stabilizer weighed out precisely beforehand, and oil droplets with aiming size are formed by mixing with stirrer, and polymerization is conducted by gradually warming mixed solution.

The ratio of monofunctional monomer to polyfunctional monomer is not particularly restricted, and, to 1 mol of monofunctional monomer, around 0.01 to 0.2 mol of polyfunctional monomer are used in the case of making relatively soft particles (base material) and around 0.2 to 0.5 mol of that in the case of making hard particles; in the case of making harder particles, polyfunctional monomer alone may be used. The polymerization initiator is also not particularly restricted, and azobis type and/or peroxide type being used commonly are used. The suspension stabilizer is also not particularly restricted, and, if possible to prevent the aggregation among oil droplets themselves, any of ionic surfactants, nonionic surfactants and polymers with amphipathic property or mixtures of these can be used.

The diameter of formed particles is also not particularly restricted and particles with appropriate diameter of 2 to 500 μm may be selected in line with the use purpose. For example, when aiming at analysis, the particle diameter is better to be 2 to 30 μm, more preferably around 2 to 10 μm. When aiming at large scale purification of nucleic acids with high purity, it is around 10 to 100 μm and, when separating the aiming product from crude stock solution, it may be 100 to 500 μm, more preferably around 200 to 400 μm. For adjusting the particle diameter, the rotational speed of stirrer may be adjusted during polymerization; when particles with small diameter are needed, the number of revolutions may be increased and, when large particles are desired, the number of revolutions may be decreased. Here, since the diluent to be used is used for adjusting pores in formed particles, the selection of diluent is particularly important. As a fundamental concept, for the solvent to be used for polymerization, adjustment is made by variously combining a solvent that is poor solvent for monomer with a solvent that is good solvent for monomer. The size of pore diameter may be selected appropriately depending on the molecular size of nucleic acids designed to separate, but it is preferable to be within a range of 500 to 4000 angstroms for the packing material for hydrophobic interaction chromatography and within a range from 1500 to 4000 angstroms for the packing material for ion exchange chromatography. In the hydrophobic interaction chromatography, for separating nucleic acids with different hydrophobicity preferable by utilizing packing materials with different hydrophobicity, respectively, the surface modification of the base material is important. The applicable hydrophobic group is not particularly restricted as long as it does not deviate from the purpose to separate nucleic acids with different hydrophobicity with packing materials with different hydrophobicity, respectively, but hydrophobic groups having one or more kinds of compounds selected from a group consisting of following compounds (a) through (c) as major components are particularly preferable.

Compounds (a): These may be of long chain or branched. Saturated hydrocarbon groups or unsaturated hydrocarbon groups with carbon atoms of 2 to 20 (however, aromatic ring may be contained in the hydrocarbon group).

Compounds (b): Compounds represented by a following structural formula 1 (however, n=0~20 and methylene group may be of straight chain or branched, m=0~3 and hydrocarbon group may be of straight chain or branched, and A is C=O group or ether group, but methylene group may be bonded directly to base material without A).

Compounds (c): Ether group of alkylene glycol with carbon atoms of 2 to 20, which consists of repeating units of 0 to 10 (however, the opposite end of functional group reacted with base material may be OH group left as it is or may be capped with alkyl group with carbon atoms of 1 to 4).

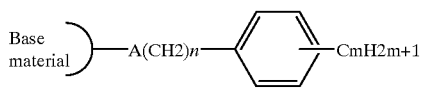

(1)

When modifying the surface using compounds dividable into three categories as above, they may be used solely or in mixture. In following, one example of different ways to use them will be explained, taking alkyl groups that belong to Compounds (a) as an example. For example, for separating compounds with high hydrophobicity such as RNA originating from *Escherichia coli* and RNA in the cells of human and animals, alkyl groups with carbon atoms of 2 to 15 are particularly suitable. Moreover, in the case of compounds with relatively low hydrophobicity such as DNAs originating from *Escherichia coli* and DNAs in the cells of human and animals, alkyl groups with carbon atoms of 4 to 18 are particularly suitable. Furthermore, in the case of compounds with low hydrophobicity like plasmids, alkyl groups with carbon atoms of 6 to 20 are suitable. Upon separating these compounds, compounds may be selected appropriately to modify the surface without being confined to said exemplification. The reason for this is that the degree of hydrophobicity of packing material varies depending on the concentration of salt in medium or the concentration of salt in eluent for adsorption. Moreover, this is because of that, even with the same functional group, the degree of hydrophobicity of packing material differs depending on the amount of the group introduced into the base material.

The pore diameter of the base material for hydrophobic interaction chromatography is particularly preferable to be 500 to 4000 angstroms, but it can be selected appropriately from said range depending on the molecular size of nucleic acids desired to separate. In general, since the retention of nucleic acids on the packing material and the adsorption capacity (sample leading) differ depending on the pore diameter, it is preferable to use a base material with large pore diameter for nucleic acids with large molecular size and a base material with small pore diameter for nucleic acids with small molecular size.

Next, one example of the methods for reacting these hydrophohic groups with base material will be described. In the case of the base material being styrene base and reacting with compounds in the first and second category, using halogen-containing compound B and/or carbonyl halide C and catalyst such as $FeCl_3$, $SnCl_2$ or $AlCl_3$, and utilizing Friedel-Craft reaction, it is possible to add directly to aromatic ring in base material as dehalogenated compound B and/or acylated compound C. In the case of the base material being particle containing halogen group, for example, using compounds with OH contained in functional group to be added, like butanol, and utilizing Williamson reaction with alkali catalyst such as NaOH or KOH, it is possible to introduce the functional group through ether bond. In the case of the functional group desired to add being amino group-containing compound, like hexylamine, it is possible to add using alkali catalyst such as NaOH or KOH and utilizing dehalogenic acid reaction. In the case of the base material containing OH group, inversely, if introducing epoxy group, halogen group or carbonyl halide group beforehand into the functional group desired to add, it is possible to introduce the functional group through ether or ester bond. In the case of the base material containing epoxy group, if reacting with compound with OH group or amino group contained in the functional group desired to add, it is possible to introduce the functional group through ether or amino bond. Moreover, in the case of the functional group desired to add containing halogen group, it is possible to add the functional group through ether bond using acid catalyst. Since the proportion of functional group to be introduced into base material is influenced by the hydrophobicity of subject product desired to separate, it cannot be restricted, but, in general, packing material with around 0.05 to 4.0 mmol of functional group added per 1 g of dried base material is suitable.

With respect to the surface modification, a method of adding the functional group through post-reaction after formation of base material (particles) has been exemplified above, but no difference exists, even if a method may be adopted, wherein the base material is formed after polymerization using monomers with said functional groups added before polymerization, thus posing no particular problem. In addition, the base material to be used may also be porous silica gel. As an example of the method of manufacturing silica gel, silane coupling may also be conducted, using a compound such as alkyltrimethoxysilane, directly onto particles manufactured according to the method described in "Latest High-Speed Liquid Chromatography", page 289 ff. (written by Toshio Nambara and Nobuo Ikegawa, published by Tokyo Hirokawa Bookstore in 1988). Or, after conducted the silane coupling using epoxy group-containing silane coupling agent, the functional group may be added according to the method aforementioned. As for the proportion of functional group to be introduced, packing material with around 0.05 to 4.0 mmol of functional group added per 1 g of dried base material is suitable.

Next, one example of the methods of separating and purifying a nucleic acid using these packing materials will be described. First, as the eluents to be used for the hydrophobic interaction chromatography of the invention, at least two types of eluents consisting of eluent A containing high-concentration of salt and eluent B containing low-concentration of salt are used. The eluting method switching stepwise from eluent A to eluent B and the gradient eluting method continuously changing the composition from eluent A to eluent B can be used. For the buffers and salts to be used in these eluents, those used usually for the hydrophobic interaction chromatography can be used. For the eluent A containing high-concentration of salt, aqueous solution with salt concentration of 1.0 to 4.5M and pH value of 6 to 8 is particularly preferable. For the eluent B containing low-concentration of salt, aqueous solution with salt concentration of 0.01 to 0.5M and pH value of 6 to 8 is particularly preferable. For the salts, ammonium sulfate and sodium sulfate can be exemplified.

In the invention, it is particularly preferable to conduct the hydrophobic interaction chromatography by combining a packing material introduced the functional group with weak hydrophobicity with a packing material introduced the functional group with strong hydrophobicity in sequence. This method is suitable particularly for the separation of plasmid. For example, in the medium cultured *Escherichia coli* in large quantity, various components different in hydrophobicity such as polysaccharides, *Escherichia coli* genome DNA, RNAs plasmids and proteins are contained, and, according to the inventors' knowledge, there are differences in the hydrophobicity even among nucleic acids themselves; proteins that become impurities have higher hydrophobicity compared with plasmids being aiming product. Hence, by connecting columns packed with various packing materials different in hydrophobicity in order from lower hydrophobicity, plasmid can be separated and purified efficiently. Concretely, after adsorbing sequentially onto the packing materials with increasingly higher hydrophobicity in order from higher hydrophobicity of components in medium, column with aiming component adsorbed alone is detached and eluted.

In the invention, it is preferable to separate and purify nucleic acids by hydrophobic interaction chromatography and ion exchange chromatography in combination for efficiently obtaining nucleic acids with high purity in large quantity. Here, for the hydrophobic interaction chromatography, packing material etc. as described above can be used. Moreover, here, as the hydrophobic interaction chromatography, it is particularly preferable to connect columns packed with various packing materials different in hydrophobicity in order from lower hydrophobicity.

The packing material to be used for ion exchange chromatography for purifying the aiming plasmic having been separated beforehand by means of hydrophobic interaction chromatography further to higher purity is preferable to have relatively large pore diameter, particularly within a range from 1500 to 4000 angstroms. How to commonly make the base material used for ion exchange chromatography is as described above, and the surface modification to introduce ion exchange groups to these base materials can be performed by publicly known method.

As the eluents to be used for the ion exchange chromatography, at least two types of eluents consisting of eluent C containing low-concentration of salt and eluent D containing high-concentration of salt are used. The eluting method switching stepwise from eluent C to eluent D and the gradient eluting method continuously changing the composition from eluent C to eluent D can be used. For the buffers and salts to be used in these eluents, those used usually for the ion exchange chromatography can be used. For the eluent C containing low-concentration of salt, aqueous solution with concentration of buffer of 10 to 50 mM and pH value of 6 to 9 is particularly preferable. For the eluent D containing high-concentration of salt, aqueous solution with 0.1 to 2M sodium salt added to eluent C is particularly preferable. For the sodium salts, sodium chloride and sodium sulfate can be mentioned.

Moreover, a component other than buffer can be contained in both eluents, and, in particular, chelating agent for bivalent metal ion, for example, ethylenediamine-tetraacetic acid is particularly in the case of separating plasmids preferable, since it can inhibit the degradation of plasmids due to DNA-degrading enzymes in the lysate of *Escherichia coli*. The concentration of chelating agent for bivalent metal ion is preferably 0.1 to 100 mM.

And, in the particularly preferable embodiment of the invention, the eluent A with high salt concentration prepared according to the method aforementioned is passed through columns of hydrophobic interaction chromatography, which are connected in order from lower hydrophobicity. After reached stationary state, medium of *Escherichia coli* etc. omitted the degrading manipulation of RNA with degrading enzyme etc. is injected into column. Successively, the eluent A is passed through to flow out the compounds that were not adsorbed in any column outside the system. Thereafter, column with aiming compound adsorbed alone is detached and aiming product is eluted by the stepwise method or gradient method. Following this, the eluent C is passed through said ion exchange column, and, after reached stationary state, the elute containing aiming product is injected as it is. Thereafter, using the eluent D, aiming product is eluted by stepwise method or gradient method to obtain purified product.

The invention provides a method for separating and purifying nucleic acids by simple manipulation. Concretely, in the preferable embodiment of the invention using columns wherein columns packed respectively with packing materials different in hydrophobicity are connected in order from lower hydrophobicity, aiming nucleic acids, in particular, long chain nucleic acids such as plasmids can be separated and purified simply in large quantity only by passing the solution from pretreatment process in the conventional manipulation. Besides, in the invention, it is also possible to separate and purify nucleic acids by passing the solution from pretreatment process that was omitted the degrading manipulation of *Escherichia coli*-originated RNA with degrading enzyme in the conventional pretreatment process directly through the columns of hydrophobic chromatography.

In the invention, if using the hydrophobic interaction chromatography and the ion exchange chromatography in combination, which is preferable in particular, it is possible to separate and purify aiming nucleic acids with high purity, in particular, long chain nucleic acids such as plasmids in large quantity by simple manipulation.

As described, according to the inventive method for separating nucleic acids, aiming products with high purity can be obtained in large quantity by simpler manipulation over conventional method.

In following, the invention will be illustrated in more detail based on the examples, but the invention is not confined to these examples.

EXAMPLE 1

(1) Preparation of packing material for hydrophobic interaction chromatography

Employing a packing material for gel filtration chromatography (G6000PW (from Tosoh Corp.)) with average particle diameter of 20 μm and average pore diameter of 2000 angstroms as the base material, the packing material for the hydrophobic interaction chromatography was prepared. A mixture of 20 g of G6000PW washed and substituted with 1,4-dioxane, 20 g of 1,4-dioxane and 1 g of 1,2-epoxybutane was stirred and mixed for 6 hours at 45° C. to obtain a packing material (hereinafter referred to as Butyl-6PW) having butyl group as a functional group of weak hydrophobicity. Similarly, a mixture of 20 g of G6000PW, 20 g of 1,4-dioxane and 1 g of 1,2-epoxyoctane was stirred and mixed for 6 hours at 45° C. to obtain a packing material (hereinafter referred to as Octyl-6PW) having octyl group as a functional group of strong hydrophobicity. Each packing material was packed into a stainless steel column with inner diameter of 7.5 mm and length of 7.5 cm.

(2) Separation of a plasmid by hydrophobic interaction chromatography

After *Escherichia coli* having pBR322 as a plasmid was cultured for 16 hours at 37° C., the medium was subjected to centrifugal separation for 20 minutes at 4° C. and 8000 rpm. The precipitated *Escherichia coli* was suspended into 10 ml of 25 mM Tris hydrochloric acid buffer (pH 7.5) containing 100 mg of lysozyme, 50 mM glucose and 10 mM ethylenediamine-tetraacetic acid (hereinafter referred to as EDTA), which was stirred and then allowed to stand for 5 minutes at room temperature to dissolve cell wall. Then, 20 ml of 0.2N sodium hydroxide solution containing 1% sodium dodecylsulfate were added thereto, and, after mixed gently, the mixture was allowed to stand for 10 minutes under cooling with ice to dissolve cytoplasmic membrane.

Next, 15 ml of 3M sodium acetate buffer (pH 5.4) were added thereto, and the mixture was stirred slowly and allowed to stand for 30 minutes under cooling with ice. Then, after subjected to centrifugal separation for 20 minutes at 4° C. and 10000 rpm, the supernatant was collected to obtain a cleared lysate of *Escherichia coli*. After equal volume of 0.1M sodium phosphate buffer (pH 7.0) containing 4M ammonium sulfate was added to the crushed liquor of *Escherichia coli*, this mixture was subjected to a hydrophobic interaction chromatography.

Into tandem columns of Butyl-6PW column and Octyl-6PW column linked in series, which were equilibrated with 0.1M sodium phosphate buffer (pH 7.0) containing 2M ammonium sulfate and 1 mM EDTA, 3 ml of the crushed liquor of *Escherichia coli* containing ammonium sulfate were injected, and then 0.1M sodium phosphate buffer (pH 7.0) containing 2M ammonium sulfate and 1 mM EDTA was fed into the tandem columns for 20 minutes at flow rate of 1 ml/min to elute the impure substances outside the columns. Following this, after detached Butyl-6PW column outside the flow path system, 0.1M sodium phosphate buffer (pH 7.0) containing 1 mM EDTA was fed for 15 minutes at flow rate of 1 ml/min into only Octyl-6PW column. As a result, a chromatogram as shown in FIG. 1 was obtained. In FIG. 1, numeral 1 shows a peak of impurities and numeral 2 shows a peak of plasmid-containing fraction. The column eluate corresponding to the peak 2 was collected and purified further by means of ion exchange interaction chromatography as shown below.

Figure 2:
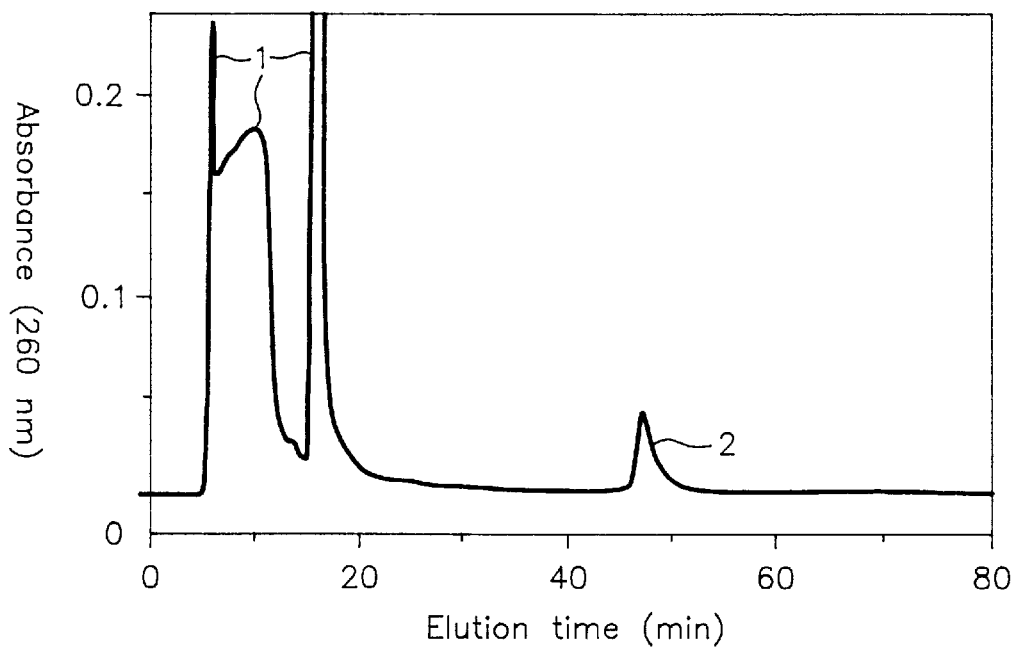
FIG. 2 is a chromatogram showing the result of separating an eluate of hydrophobic interaction chromatography by means of ion exchange chromatography in Example 1.
Figure 3:
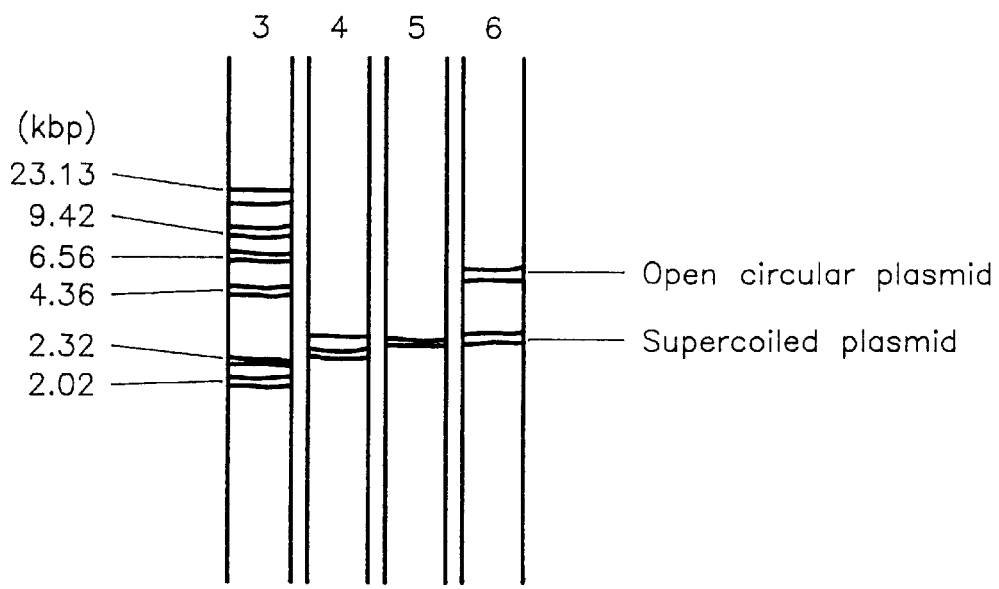
FIG. 3 is a schematic diagram of the images of gel electrophoresis showing the results of purity assay of plasmid fractions obtained in Example 1 and Comparative Example 1.

(3) Separation of a plasmid by a combined use of hydrophobic interaction chromatography and ion exchange chromatography As a packed column for the ion exchange chromatography, DEAE-5PW (trade name, from Tosoh Corp., inner diameter of 7.5 mm, length of 7.5 cm) was used. Into DEAE-5PW column equilibrated with 20 mM Tris hydrochloric acid buffer (pH 7.5) containing 0.6M sodium chloride and 1 mM EDTA, 3 ml of plasmid fraction was injected, and then 20 mM Tris hydrochloric acid buffer (pH 7.5) containing 0.6M sodium chloride and 1 mM EDTA was fed into the column for 35 minutes at flow rate of 1 ml/min to elute the impure substances outside the column. Then, the elution was conducted by a gradient method wherein the concentration of sodium chloride in 20 mM Tris hydrochloric acid buffer (pH 7.5) containing 1 mM EDTA was changed continuously from 0.6M to 0.8M over 30 minutes at flow rate of 1 ml/min. As a result, a chromatogram as shown in FIG. 2 was obtained. In FIG. 2, numeral 1 shows peaks of impurities and numeral 2 shows a peak of plasmid-containing fraction. The column eluate corresponding to the peak 2 was collected and the purity was examined by agarose gel electrophoresis. When dyeing the gel after the electrophoresis with ethidium bromide, electrophoretic images as shown in FIG. 3 were obtained. In FIG. 3, numeral 3 shows a DNA size marker, numeral 5 shows a plasmid fraction obtained by the present purifying method, and numeral 6 shows an electrophoretic image of commercial purified pBR322. As evident from the diagram, high-purity supercoil type plasmid could be obtained by simple manipulation according to the present purifying method.

Comparative Example 1

For comparison, purification of a plasmid pBR322 was conducted from the cleared lysate of *Escherichia coli* by means of ion exchange interaction chromatography alone.

Figure 4:
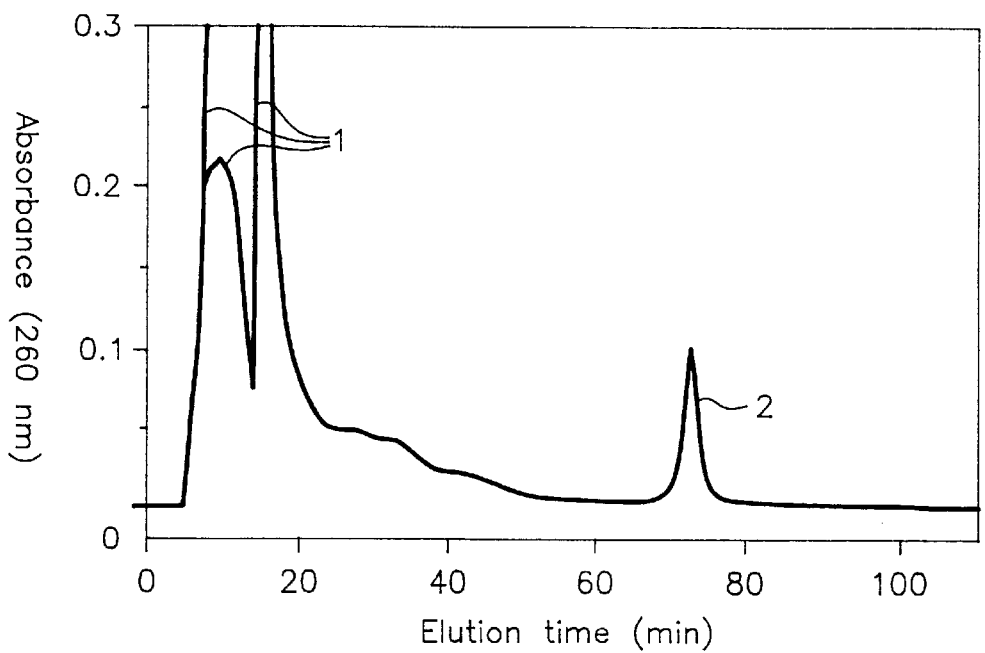
FIG. 4 is a chromatogram showing the result of separating a cleared lysate of *Escherichia coli* separated by means of ion exchange chromatography in Comparative Example 1.

After prepared the cleared lysate of *Escherichia coli* similarly to the Example, equal volume of 20 mM Tris hydrochloric acid buffer (pH 7.5) was added thereto to make a sample for the ion exchange chromatography. Into the previous DEAE-5PW column equilibrated with 20 mM Tris hydrochloric acid buffer (pH 7.5) containing 0.6M sodium chloride and 1 mM EDTA, 3 ml of sample were injected, and then 20 mM Tris hydrochloric acid buffer (pH 7.5) containing 0.6M sodium chloride and 1 mM EDTA was fed into the column for 60 minutes at flow rate of 1 ml/min to elute the impure substances outside the column. Next, elution was conducted by the gradient method similarly to the Example. As a result, a chromatogram as shown in FIG. 4 was obtained. In FIG. 4, numeral 1 shows peaks of impurities and numeral 2 shows a peak of plasmid-containing fraction. The column effluent corresponding to the peak 2 was collected and the purity was examined by agarose gel electrophoresis. As a result, electrophoretic images as shown in FIG. 3 were obtained. In FIG. 3, numeral 3 shows a DNA size marker, numeral 4 shows a plasmid fraction obtained in the Comparative Example, numeral 5 shows a plasmid fraction obtained in the Example 1, and numeral 6 shows an electrophoretic image of commercial purified pBR322. Many impurities were contained in the plasmid fraction obtained by means of ion exchange chromatography alone.

EXAMPLE 2

(1) Preparation of packing materials for hydrophobic interaction chromatography

Employing a packing material for gel filtration chromatography (G6000 PW (from Tosoh Corp.)) with average particle diameter of 20 μm and average pore diameter of 2000 angstroms as the base material, the packing material for the hydrophobic interaction chromatography was prepared. A mixture of 20 g of G6000 PW washed and substituted with 1,4-dioxane, 20 g of 1,4-dioxane, 1 g of 1,2-epoxyoctane and 0.5 ml of boron trifluoride as catalyst was stirred and mixed for 6 hours at 45° C. to obtain a packing material (hereinafter referred to as Octyl-6 PW) having octyl group for adsorbing plasmid and for hydrophobic interaction chromatography.

Next, employing a packing material for gel filtration chromatography (G5000 PW (from Tosoh Corp.)) with average particle diameter of 20 μm and average pore diameter of 950 angstroms as the base material, a packing material with weak hydrohobicity was prepared. A mixture of 20 g of G5000 PW, 20 g of 1,4-dioxane, 1 g of 1,2-epoxybutane and 0.5 ml of boron trifluoride as catalyst was stirred and mixed for 6 hours and at 45° C. to obtain a packing material (hereinafter referred to as Butyl-5 PW) having butyl group for adsorbing RNAs and proteins and for hydrophobic interaction chromatography. Each packing material was packed into a stainless steel column with inner diameter of 7.5 mm and length of 7.5 cm.

(2) Separation of a plasmid by a combined use of hydrophobic interaction chromatography and ion exchange chromatography—separation by hydrophobic interaction chromatography After *Escherichia coli* having pBR 322 as a plasmid was cultured for 16 hours at 37° C., the medium was subjected to centrifugal separation for 20 minutes at 4° C. and 8000 rpm. The precipitated *Escherichia coli* was suspended into 10 ml of 25 mM Tris hydrochloric acid buffer (pH 7.5) containing 100 mg of lysozyme, 50 mM glucose and 10 mM ethylenediamine tetraacetate (hereinafter referred to as EDTA), which was stirred and then allowed to stand for 5 minutes at room temperature to dissolve cell wall. Then, 20 ml of 0.2N sodium hydroxide solution containing 1% sodium dodecylsulfate were added thereto, after mixed gently, the mixture was allowed to stand for 10 minutes under cooling with ice to dissolve cytoplasmic membrane.

Next, 15 ml of 3M sodium acetate buffer (pH 5.4) were added thereto, and the mixture was stirred slowly and allowed to stand for 30 minutes under cooling with ice. Then, after subjected to centrifugal separation for 20 minutes at 4° C. and 10000 rpm, the supernatant was collected to obtain a cleared lysate of *Escherichia coli*. After equal volume of 0.1M sodium phosphate buffer (pH 7.0) containing 4M ammonium sulfate was added to the cleared lysate of *Escherichia coli*, this mixture was subjected to a hydrophobic interaction chromatography.

Figure 5:
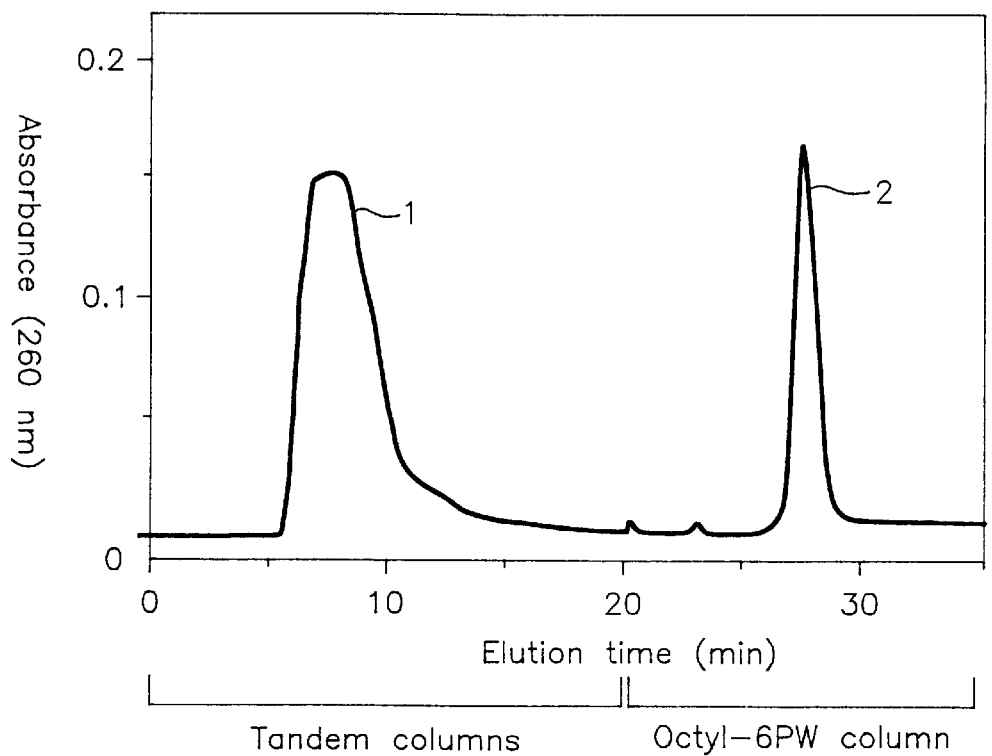
FIG. 5 is a chromatogram showing the result of separating a cleared lysate of *Escherichia coli* by means of hydrophobic interaction chromatography in Example 2.

Into tandem columns of Butyl-5 PW column and Octyl-6 PW column linked in series, which were equilibrated with 0.1M sodium phosphate buffer (pH 7.0) containing 2M ammonium sulfate and 1 mM EDTA, 3 ml of the cleared lysate of *Escherichia coli* containing ammonium sulfate were injected, and then 0.1M sodium phosphate buffer (pH 7.0) containing 2M ammonium sulfate and 1 mM EDTA was applied into the tandem columns for 20 minutes at flow rate of 1 ml/min to elute the impure substances outside the columns. Following this, after detached Butyl-5t PW column outside the flow path system, 0.1M sodium phosphate buffer (pH 7.0) containing 1 mM EDTA was fed into only Octyl-6 PW column for 15 minutes at flow rate 1 ml/min. As the result, chromatogram as shown in FIG. 5 was obtained. In FIG. 5, numeral 1 shows a peak of impurities and numeral 2 shows a peak of plasmid-containing fraction. The column effluent corresponding to the peak 2 was collected and purified further by means of ion exchange chromatography as shown below.

(3) Preparation of a packing material for ion chromatography

This was prepared by the way described below, employing a packing material (G6000 PW (from Tosoh Corp.)) for gel filtration chromatography with average particle diameter of 20 μm and average pore diameter of 2000 angstroms as base material. A mixture of 20 g of G6000 PW washed thoroughly with pure water, 40 g of pure water, 10 g of epichlorohydrin, 10 g of diethylaminoethanol and 5 g of NaOH was stirred and mixed for twenty-four hours at 40° C. to obtain anion exchanger (hereinafter referred to as DEAE-6 PW) having total ion-exchange capacity of 0.05 meq/ml-gel for purifying plasmid.

This packing material was packed into a stainless steel column with inner diameter of 7.5 mm and length of 7.5 cm for ion-exchange chromatography.

(4) Separation of a plasmid by a combined use of hydrophobic interaction chromatography and ion exchange chromatography After 3 ml of a plasmid fraction was injected into a DEAE-6 PW column equilibrated with 20 mM Tris hydrochloric acid buffer (pH 7.5) containing 0.6M sodium chloride and 1 mM EDTA, 20 mM Tris hydrochloric acid buffer (pH 7.5) containing 0.6M sodium chloride and 1 mM EDTA was fed into the column for 35 minutes at flow rate of 1 ml/min to elute impure substances outside the column.

Figure 6:
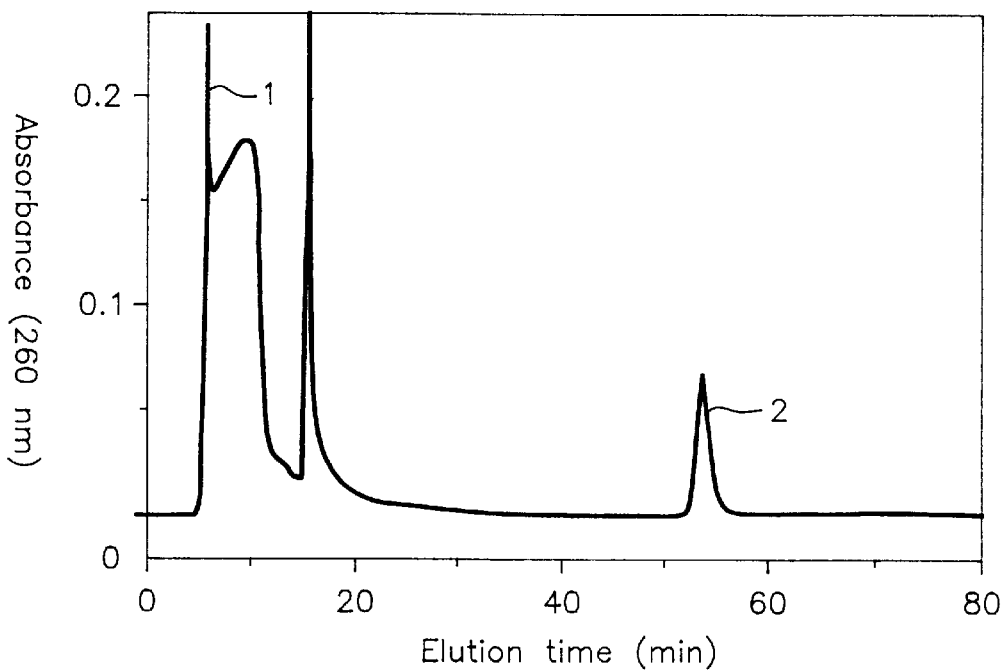
FIG. 6 is a chromatogram showing the result of separating an eluate of hydrophobic interaction chromatography by means of ion exchange chromatography in Example 2.

Then, the elution was conducted by a gradient method wherein the concentration of sodium chloride in 20 mM Tris hydrochloric buffer (pH 7.5) containing 1 mM EDTA was changed continuously from 0.6M to 0.8M over 30 minutes at flow rate of 1 ml/min. As a result, a chromatogram as shown in FIG. 6 was obtained. In FIG. 6, numeral 1 shows peaks of impurities and numeral 2 shows a peak of plasmid-containing fraction. The column effluent corresponding to the peak 2 was collected and the purity was examined by agarose gel electrophoresis. When dying the gel after the electrophoresis with ethidium bromide, a supercoil type plasmid of high purity could be obtained in the present Example.

Comparative Example 2

For comparison, purification of a plasmid pBR 322 from the cleared lysate of *Escherichia coli* was conducted by ion-exchange chromatography alone.

After the cleared lysate of *Escherichia coli* was prepared like as in Example 2, equal volume of 20 mM Tris hydrochloric acid buffer (pH 7.5) was added thereto to make a sample. Into the above-mentioned DEAE-6 PW column equilibrated with 20 mM Tris hydrochloric acid buffer (pH 7.5) containing 0.6M sodium chloride and 1 mM EDTA, 3 ml of the sample were injected, and thereafter 20 mM Tris hydrochloric acid buffer (pH 7.5) containing 0.6M sodium chloride and 1 mM EDTA was fed into the column for 60 minutes at flow rate of 1 ml/min to elute impure substances outside the column.

Figure 7:
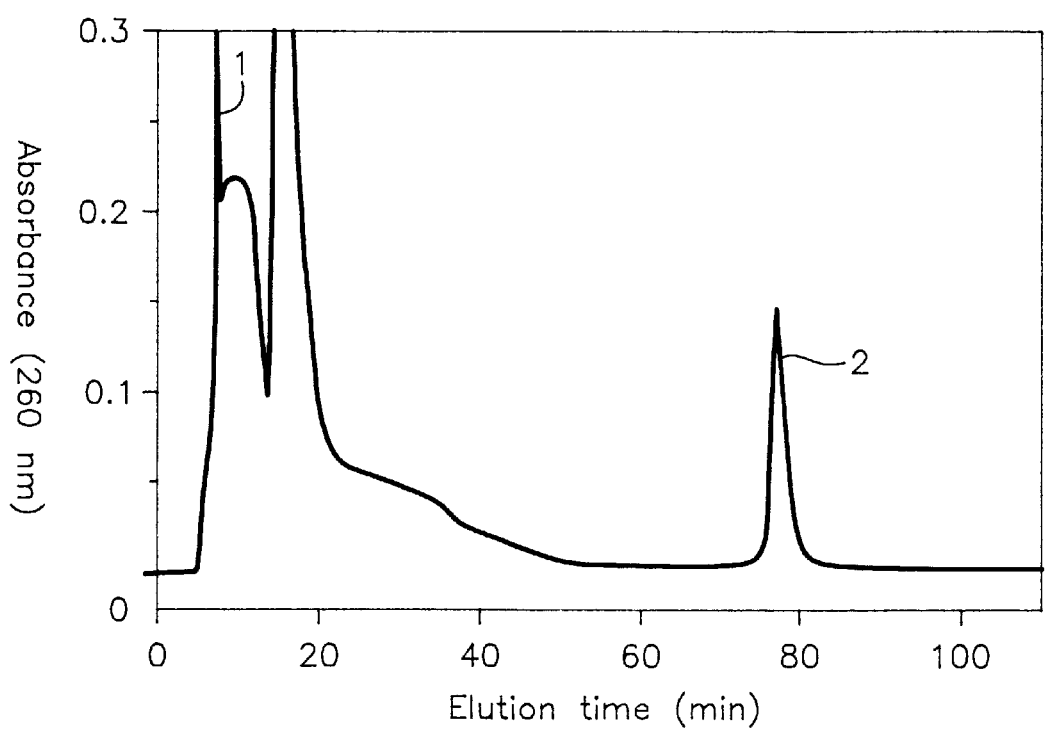
FIG. 7 is a chromatogram showing the result of separating a cleared lysate of *Escherichia coli* by means of ion exchange chromatography in Comparative Example 2.

Then, the elution was carried out by the gradient method likewise as in Example. As the result, a chromatogram shown in FIG. 7 was obtained. In FIG. 7, numeral 1 shows peaks of impurities and numeral 2 shows a peak of fraction containing plasmid. The column effluent corresponding to the peak of numeral 2 was collected and the purity was examined by agarose-gel electrophoresis. As the result, the plasmid fraction obtained by ion-exchange chromatography alone was recognized to contain a lot of impurities.

EXAMPLE 3

Adsorption capacity of a plasmid

Adsorption capacity of the packing material for hydrophobic interaction chromatography employed in Example 2, Octyl-6 PW was examined. Into a stainless steel column with inner diameter of 6.0 mm and length of 10 mm, the gel was packed and 0.1M sodium phosphate buffer (pH 7.0) containing 2.0M ammonium sulfate and 0.1 mM EDTA was fed thereinto for 20 minutes at flow rate of 0.64 ml/min to make the column equibrated. Then. about 0.4 mg/ml plasmid pUC 19 (2686 base pairs) of 4 ml was injected into the column and non-adsorption fraction which was not adsorbed onto the column was collected.

Next, by changing the eluent to 0.1M sodium phosphate buffer (pH 7.0) containing 0.1 mM EDTA, plasmid adsorbed onto the column was eluted to collect the adsorption fraction.

Following this, basing on the calibration curve of plasmid pUC 19 (an equation which shows the relationship between the injected quantity of plasmid pUC 19 and area of chromatograph) which was previously obtained by a gel filtration chromatography on TSK gel DNA-PW column (from Tosoh Corp.), the quantity of plasmid pUC 19 contained in every fraction was determined to calculate adsorption capacity per 1 ml of gel and recovery. With respect to the packing material for ion exchange chromatography, DEAE-6 PW, the adsorption capacity was likewise examined, too.

Except adsorption and disorption eluents all of the others were conducted under the same condition. As the result, adsorption quantity of Octyl-6 PW was 1.1 mg/ml and adsorption quantity of DEAE-6 PW was 2.4 mg/ml. Further, recoveries thereof were 90.3% and 77.3%, respectively.

Comparative Example 3

For comparison, a packing material of which pore diameter is smaller than that of Octyl-6 PW was prepared and the comparison of adsorption quantity was tested. The preparation was made by employing a packing material for gel filtration chromatography (G5000 PW (from Tosoh Corp.)) with average particle diameter of 20 μm and average pore diameter of 950 angstroms as a base material. A mixture of 20 g of G5000 PW, 20 g of 1,4-dioxane, 1 g of 1,2-epoxyoctane and 0.5 ml of boron trifluoride as catalyst were stirred and mixed for 6 hours at 45° C. to obtain Octyl-5 PW having octyl group.

With respect to packing material for ion-exchange chromatography, commercially available DEAE-5 PW (average particle diameter of 20 μm, average pore diameter of 880 angstroms, from Tosoh Corp.) of which pore diameter is smaller than that of DEAE-6 PW was employed, too. The determination of adsorption capacity of plasmid was conducted likewise as in the above-mentioned Example. As a result, adsorption capacity of Octyl-5 PW was 0.6 mg/ml and adsorption capacity of DEAE-5 PW was 1.2 mg/ml. Recoveries thereof were 89.9% and 60.6%, respectively.

As evident from the above results of Example 3 and Comparative Example, those having larger pore diameter can submit good results for long chain nucleic acids such as plasmid in both adsorption capacity and recovery.

What is claimed is:

1. A method for separating a plasmid from a solution containing the plasmid together with contaminants selected from a group consisting of proteins, RNAs, DNAs and mixtures thereof, using hydrophobic interaction chromatography, comprising the steps of:

a) selecting a first column material for a first hydrophobic interaction chromatography that does not adsorb the plasmid at a salt concentration at which protein and RNA are adsorbed, b) selecting a second column material for a second hydrophobic interaction chromatography that adsorbs the plasmid at a salt concentration at which the first column material adsorbs protein and RNA and the first column material does not adsorb the plasmid, c) injecting the solution containing the plasmid and contaminants into a first column containing the first column material to adsorb protein and RNA onto the first column material and form an eluate containing the plasmid and DNA, d) injecting the eluate containing the plasmid and DNA from the first column into a second column containing the second column material to adsorb the plasmid and DNA onto the second column material, and e) eluting the adsorbed plasmid from the second column material with an eluent containing salt of a concentration at which the plasmid is eluted from the second column material.

2. The method of claim 1, wherein the average particle diameter of the column material for hydrophobic interaction chromatography is 2 to 500 μm.

3. The method of claim 1, wherein the average pore diameter of the column material for hydrophobic interaction chromatography is 500 to 4000 angstroms.

4. A method for separating a plasmid from a solution containing the plasmid, together with contaminants selected from a group consisting of proteins, RNAs, DNAs and mixtures thereof, using hydrophobic interaction chromatography, comprising the steps of a) selecting a first column material for a first hydrophobic interaction chromatography that does not adsorb the plasmid at a salt concentration at which the protein and RNA are adsorbed, b) selecting a second column material for a second hydrophobic interaction chromatography that adsorbs the plasmid at a salt concentration at which the first column material adsorbs protein and RNA and the first column material does not adsorb the plasmid, c) preparing a tandem column by connecting in series a first column containing the first column material to a second column containing the second column material, d) injecting the solution containing the plasmid and contaminants into the tandem column to adsorb protein and RNA onto the first column material and plasmid and DNA onto the second column material, e) breaking the connection between the first column and the second column, and f) eluting the adsorbed plasmid from the second column material with an eluent containing salt of a concentration at which plasmid is eluted from the second column material.

5. The method of claim 4, wherein the average particle diameter of the column material for hydrophobic interaction chromatography is 2 to 500 μm.

6. The method of claim 4, wherein the average pore diameter of the column material for hydrophobic interaction chromatography is 500 to 4000 angstroms.

7. A method for separating a plasmid from a solution containing the plasmid, together with contaminants selected from a group consisting of proteins, RNAs, DNAs and mixtures thereof, using hydrophobic interaction chromatography and ion exchange chromatography, comprising the steps of a) selecting a first column material for a first hydrophobic interaction chromatography that does not adsorb the plasmid at a salt concentration at which protein and RNA are adsorbed, b) selecting a second column material for a second hydrophobic interaction chromatography that adsorbs the plasmid at a salt concentration at which the first column material adsorbs protein and RNA and the first column material does not adsorb the plasmid, c) injecting the solution containing the plasmid and contaminants into a first column containing the first column material to adsorb the protein and RNA onto the first column material and form an eluate containing the plasmid and DNA, d) injecting the eluate, containing the plasmid and DNA, from the first column into a second column containing the second column material to adsorb the plasmid and DNA onto the second column material, e) eluting the adsorbed plasmid from the second column material with an eluent containing salt of a concentration at which the plasmid is eluted from the second column material in an eluate, f) injecting the eluate into a column for ion exchange chromatography containing a material for ion exchange chromatography at a salt concentration at which the material for ion exchange chromatography adsorbs the plasmid, to adsorb the plasmid onto the material for ion exchange chromatography, and g) eluting the adsorbed plasmid from the material for ion exchange chromatography with an eluent containing salt of a concentration at which the plasmid is eluted from the material for ion exchange chromatography.

8. The method of claim 7, wherein the average particle diameter of the material for hydrophobic interaction chromatography is 2 to 500 $\mu$m.

9. The method of claim 7, wherein the average pore diameter of the material for hydrophobic interaction chromatography is 500 to 4000 angstroms.

10. The method of claim 7, wherein the average particle diameter of the material for the ion exchange chromatography is 2 to 500 $\mu$m.

11. The method of claim 7, wherein the average pore diameter of the material for ion exchange chromatography is 1500 to 4000 angstroms.

12. A method for separating a plasmid from a solution containing the plasmid, together with contaminants selected from a group consisting of protein, RNA, DNA and mixtures thereof, using hydrophobic interaction chromatography and ion exchange chromatography, comprising the steps of a) selecting a first column material for a first hydrophobic interaction chromatography that does not adsorb the plasmid at a salt concentration at which protein and RNA are adsorbed, b) selecting a second column material for a second hydrophobic interaction chromatography that adsorbs the plasmid at a salt concentration at which the first column material adsorbs protein and RNA and the first column material does not adsorb the plasmid, c) preparing a tandem column by connecting in series a first column containing the first column material to a second column containing the second column material, d) injecting the solution containing the plasmid and contaminants into the tandem column to adsorb the protein and RNA onto the first column material and plasmic and DNA onto the second column material, e) beaking the connection between the first column and the second column, f) eluting the adsorbed plasmid from the second column material with an eluent containing salt of a concentration at which the plasmid is eluted from the second column material in an eluate, g) injecting the eluate containing the plasmid from the second column into a column for the ion exchange chromatography containing a meterial for ion exchange chromatography, at a salt concentration at which the material for ion exchange chromatography adsorbs plasmid, to adsorb the plasmid onto the material for the ion exchange chromatography, and h) eluting the adsorbed plasmid from the material for ion exchange chromatography with an eluent containing salt of a concentration at which the plasmid is eluted from the material for ion exchange chromatography.

13. The method of claim 12, wherein the average particle diameter of the material for hydrophobic interaction chromatography is 2 to 500 $\mu$m.

14. The method of claim 12, wherein the average pore diameter of the material for hydrophobic interaction chromatography is 500 to 4000 angstroms.

15. The method of claim 12, wherein the average particle diameter of the material for ion exchange chromatography is 2 to 500 $\mu$m.

16. The method of claim 12, wherein the average pore diameter of the material for ion exchange chromatography is 1500 to 4000 angstroms.

* * * * *